(12) United States Patent
Bonny et al.

(10) Patent No.: US 10,792,109 B2
(45) Date of Patent: Oct. 6, 2020

(54) METHODS FOR LOCATING AND TRACKING A TOOL AXIS

(71) Applicant: THINK SURGICAL, INC., Fremont, CA (US)

(72) Inventors: Daniel Patrick Bonny, Fremont, CA (US); Joel Zuhars, Fremont, CA (US); Nathan A. Netravali, Palo Alto, CA (US)

(73) Assignee: Think Surgical, Inc., Fremont, CA (US)

( * ) Notice: Subject to any disclaimer, the term of this patent is extended or adjusted under 35 U.S.C. 154(b) by 37 days.

(21) Appl. No.: 15/548,138

(22) PCT Filed: Mar. 7, 2016

(86) PCT No.: PCT/US2016/021205
§ 371 (c)(1),
(2) Date: Aug. 2, 2017

(87) PCT Pub. No.: WO2016/141378
PCT Pub. Date: Sep. 9, 2016

(65) Prior Publication Data
US 2018/0014888 A1 Jan. 18, 2018

Related U.S. Application Data

(60) Provisional application No. 62/128,857, filed on Mar. 5, 2015.

(51) Int. Cl.
*A61B 34/20* (2016.01)
*A61B 17/00* (2006.01)
(Continued)

(52) U.S. Cl.
CPC .............. *A61B 34/20* (2016.02); *A61B 17/15* (2013.01); *A61B 17/17* (2013.01); *A61B 34/30* (2016.02);
(Continued)

(58) Field of Classification Search
CPC .......... A61B 34/20; A61B 2017/00725; A61B 34/30; A61B 34/32; A61B 34/35;
(Continued)

(56) References Cited

U.S. PATENT DOCUMENTS 5,921,992 A 7/1999 Costales et al.
5,987,960 A 11/1999 Messner et al.
(Continued)

FOREIGN PATENT DOCUMENTS

CN 102792305 A 11/2012
JP 2001-500775 A 1/2001
(Continued)

OTHER PUBLICATIONS

International Search Report dated Jul. 25, 2016 for International Application No. PCT/US2016/021205 filed Mar. 7, 2016.
(Continued)

*Primary Examiner* — Robert R Raevis
(74) *Attorney, Agent, or Firm* — Blue Filament Law PLLC

(57) ABSTRACT

A calibration device is provided having a body with an exterior surface configured for placement about a tool such that the body rotates about a tool axis. One or more fiducial marker is positioned on the exterior surface and in communication with a tracking system. A fixed fiducial marker array is provided that is also in communication with the tracking system. A calibration tool defines the tool axis relative to the fiducial marker array. A surgical system is also provided with a tracking module that calculates a center
(Continued)

point of the rotation or a normal vector to the circular path to define a tool axis orientation. A method of using the surgical system and defining a tool axis relative to a fiducial marker array is provided. A system for defining a robot link orientation or tracking a tool a medical procedure and a fiducial marker array are provided.

17 Claims, 7 Drawing Sheets

(51) Int. Cl.
*A61B 34/30* (2016.01)
*A61B 90/00* (2016.01)
*A61B 17/15* (2006.01)
*A61B 17/17* (2006.01)

(52) U.S. Cl.
CPC ............... *A61B 2017/00725* (2013.01); *A61B 2034/207* (2016.02); *A61B 2034/2055* (2016.02); *A61B 2090/3983* (2016.02)

(58) Field of Classification Search
CPC ............ A61B 34/37; A61B 2090/3983; A61B 2034/2055; A61B 2035/207; A61B 17/15; A61B 17/17
USPC .............. 73/1.79, 1.81, 1.75; 702/85, 94, 96
See application file for complete search history.

(56) References Cited

U.S. PATENT DOCUMENTS

| | | | |
|---|---|---|---|
| 6,033,415 A | 3/2000 | Mittelstadt et al. | |
| 6,112,113 A | 8/2000 | Van Der Brug et al. | |
| 7,043,961 B2 | 5/2006 | Pandey et al. | |
| 9,724,165 B2 | 8/2017 | Arata et al. | |
| 2003/0209096 A1 | 11/2003 | Pandey et al. | |
| 2005/0074304 A1* | 4/2005 | Couture | A61B 17/1703 408/110 |
| 2006/0104707 A1 | 5/2006 | Neubauer et al. | |
| 2006/0285641 A1* | 12/2006 | Scherch | A61B 5/064 378/65 |
| 2008/0154262 A1 | 6/2008 | Brundobler et al. | |
| 2009/0247861 A1* | 10/2009 | Manus | A61B 90/36 600/424 |
| 2011/0263971 A1 | 10/2011 | Nikou et al. | |
| 2012/0323111 A1 | 12/2012 | Jain et al. | |
| 2014/0214358 A1 | 7/2014 | Ji | |
| 2014/0275955 A1 | 9/2014 | Crawford et al. | |
| 2017/0258532 A1 | 9/2017 | Shalayev et al. | |

FOREIGN PATENT DOCUMENTS

| | | |
|---|---|---|
| JP | 2004-050356 A | 2/2004 |
| JP | 2004-529679 A | 9/2004 |
| JP | 2009-537230 A | 10/2009 |
| JP | 2013-039643 A | 2/2013 |
| JP | 2013-524952 A | 6/2013 |
| JP | 2015-502186 A | 1/2015 |
| WO | 02/061371 * | 8/2002 |

OTHER PUBLICATIONS

Extended European Search Report dated Jan. 17, 2019 for International Application No. PCT/US2016/021205 filed Mar. 7, 2016.
U.S. Appl. No. 91/527,762, dated Oct. 13, 2015, Ji.
Office Action issued in corresponding Japanese Pat. Appln. No. 2017-534924, dated Feb. 10, 2020.

* cited by examiner

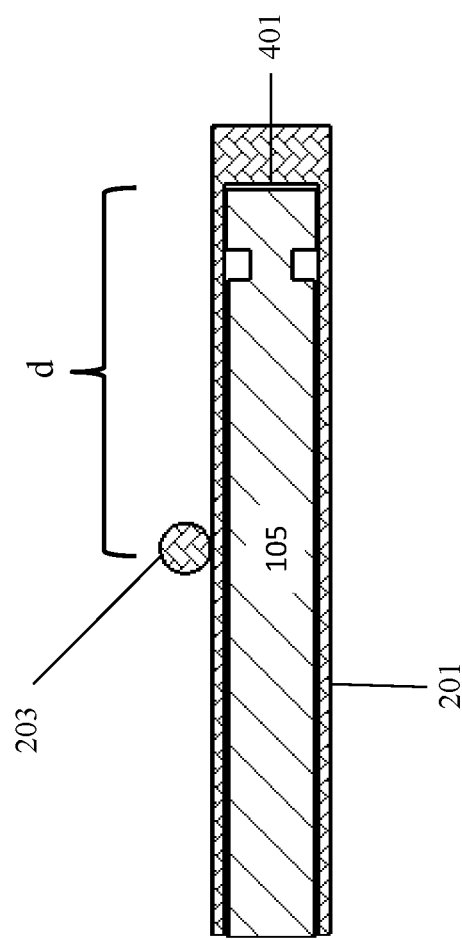
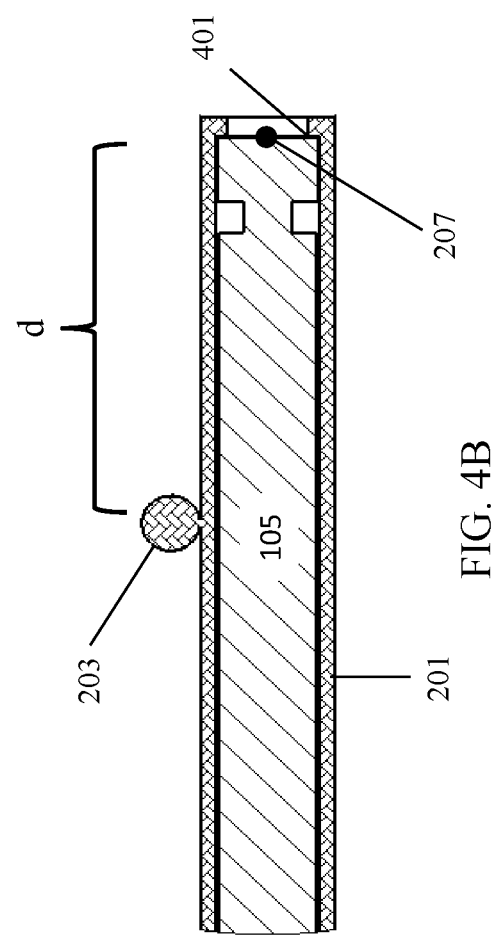

METHODS FOR LOCATING AND TRACKING A TOOL AXIS

RELATED APPLICATIONS

This application claims priority benefit of U.S. Provisional Application Ser. No. 62/128,857 filed 5 Mar. 2015; the contents of which are hereby incorporated by reference.

FIELD OF THE INVENTION

The present invention generally relates to the field of computer-aided surgical systems, and more specifically to a new and useful device and method for calibrating a tool relative to a tracking system.

BACKGROUND OF THE INVENTION

Computer-assisted surgical systems are widely used to aid surgeons in performing a variety of medical procedures. One such example is the ROBODOC™ Surgical System (Think Surgical™, Fremont, Calif.) that assists a surgeon in preparing the femoral canal in total hip arthroplasty (THA). In order to prepare the canal with submillimeter accuracy, both the tool center point (TCP) and the center axis of the tool must be accurately calibrated with respect to a robotic coordinate frame as well as any other tracking system coordinate frame. The tracking system may also be used to locate and track other objects in the operating room such as the anatomy of interest or other medical devices. Therefore the relationships between all of the tracked objects may be coalesced to improve or aid in a medical procedure in a dynamic manner.

Tracking systems typically include multiple receivers that detect energy from a set of passive or active fiducial markers. In order to define the relationship between the tool orientation and tip position relative to an array of tracked fiducial markers, a calibration procedure must be performed. There are many different methods of calibrating an array of fiducial markers relative to a tool tip position and orientation, however the processes are usually time-consuming, costly and/or not accurate enough for a particular surgical procedure.

One existing method of calibration is to manufacture the array at a precise position and orientation on the tool followed by a factory calibration step. However, the method requires precise placement of the array on every tool that may be used in a surgical setting, increasing overall costs. An alternative method is to calibrate the tool relative to the array within the operating room. A digitizer either mechanically or optically tracked is manually positioned to collect a number of points on the tool to define the geometric relationship between the tool and the array. However, when calibrating an optically-tracked cutting tool using single measurements, tracking systems are insufficiently accurate to be used as a calibration device based on the inherent error of the system. Additionally, the digitizing process is laborious for the user and increases overall operating time.

Once the relationship between the fiducial marker array and the tool are known, the position and orientation of the tool may be accurately tracked during a procedure. However, another problem with traditional tracking systems is an inherent error in locating each of the fiducial markers in three-dimensional space during tracking, which may affect tracking accuracy. The errors may be a function of the triangulation, sampling times, manufacturing errors in the geometric relationship between fiducial markers, and the fact that the markers are stationary with respect to one another. Considering the need for very precise surgical procedures, any method that can improve the accuracy of the tracking system is highly desirable.

Thus there is a need in the art for a calibration device that can quickly and accurately define a tool tip position and orientation relative to a tracking array in computer-assisted surgical systems and other robotic applications that require a high level of precision. There is a further need to improve the accuracy of the tracking to improve the results of a surgical procedure and the reliability of the surgical system, or for other robotic applications.

SUMMARY OF THE INVENTION

A calibration device is provided that has a body with an exterior surface. The body is configured for placement about a tool having a tool axis such that the body rotates about the tool axis. At least one fiducial marker is positioned on an exterior surface of the body and is in communication with a tracking system. A fixed fiducial marker array is provided that is also in communication with the tracking system. A calibration tool defines the tool axis relative to the fiducial marker array.

A surgical system is also provided that includes a tool and a tracking module. A fiducial marker array is fixed to the tool and in communication with the tracking module. A calibration device includes a body with at least one fiducial marker positioned on the body, where the body is configured for placement about the tool such that the body rotates about a tool axis. In response to the rotation of the body one or more circular paths are generated by the at least one fiducial marker that are tracked by the tracking module, and the tracking module calculates at least one of a center point of the rotation or a normal vector to the circular path to define a tool axis orientation relative to the fiducial marker array fixed to said tool and to said tracking module. A method of using the surgical system includes the calculation of average of the normal vectors to the circular paths traced by two or more rotated fiducial markers, the average of the normal vectors between the center points of the circular paths traced by the two or more rotated fiducial markers, or the average of the two aforementioned options.

A method for defining a tool axis relative to a fiducial marker array is provided that includes the fixation of a fiducial marker array to a surgical tool. A calibration device with at least one fiducial marker is attached on the tool. A calibration device is attached about the tools axis. The rotation of said at least one fiducial marker is tracked with a tracking module. A normal vector and a center point are calculated from one or more circular paths traced by the fiducial marker rotation to define the tool axis orientation relative to the fiducial marker array.

A system for defining a robot link orientation is also provided that includes a distal link and a proximal link attached to the distal link. A tracking module and a set of fiducial markers are placed on the distal link such that three fiducial markers from the set of fiducial markers are visible to the tracking module such that a processor can define a first coordinate system on the distal link.

A system for tracking a tool to aid in a medical procedure is also providing that includes a surgical tool equipped with a tracking module. A rotating body coincident about an axis of the tool is provided. The rotating body includes at least one fiducial marker such that the tracking module records a position of the at least one fiducial marker as the at least one fiducial marker rotates about the tool axis.

A fiducial marker array for tracking an object in the context of surgical robot is provided that includes a rigid body and at least one fiducial marker in communication with a tracking module that rotates creating a circular path on a region of the rigid body whereby the at least one fiducial marker is offset a distance from the center of rotation of the fiducial marker.

BRIEF DESCRIPTION OF THE DRAWINGS

The present invention is further detailed with respect to the following drawings that are intended to show certain aspects of the present invention, but should not be construed as a limit on the practice of the present invention.

FIGS. 4A and 4B are a cross-section views of a calibration device defining a tool tip center point relative to fiducial marker array in accordance with embodiments of the invention;

DETAILED DESCRIPTION OF THE INVENTION

Figure 1:
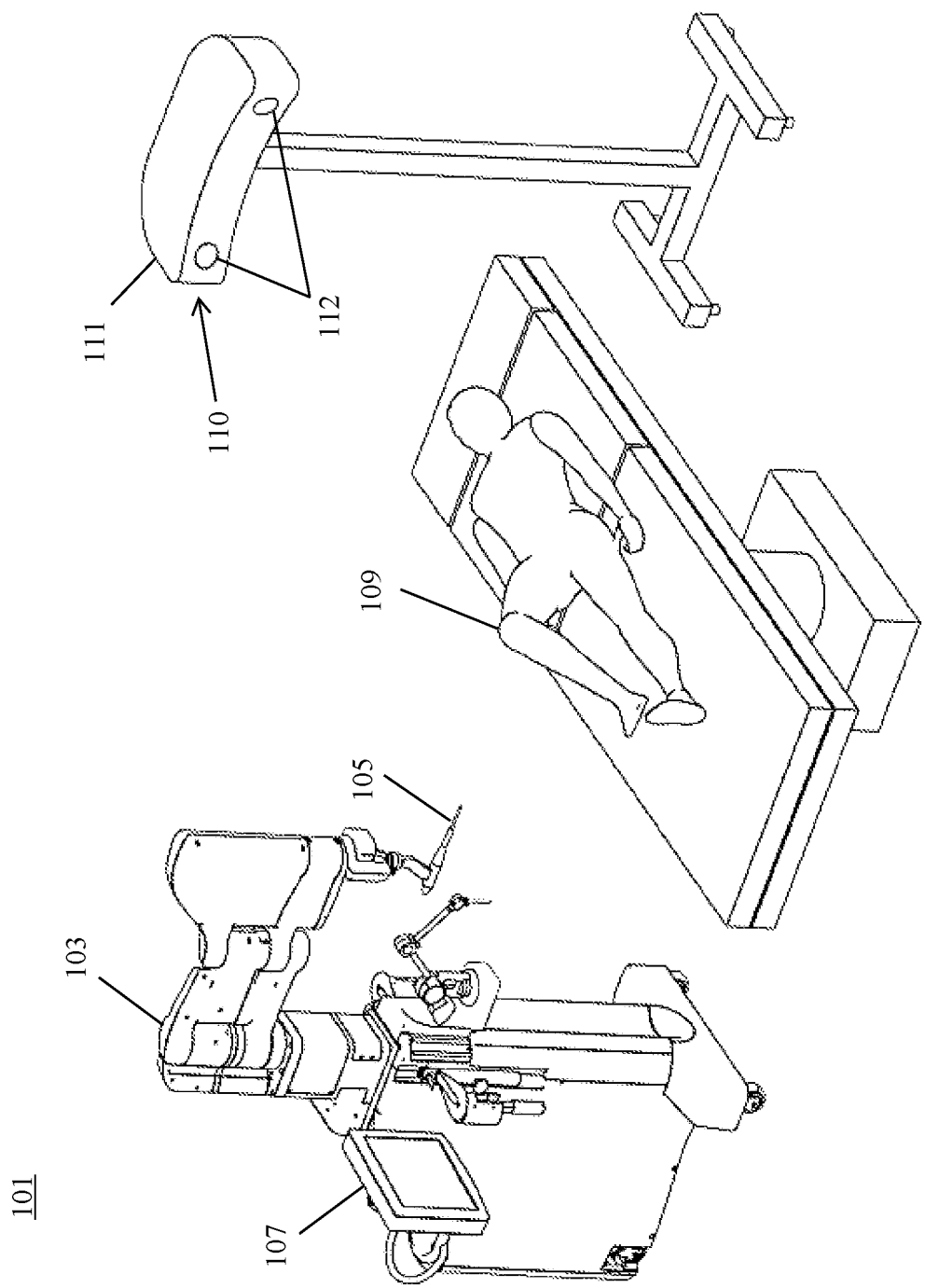
FIG. 1 illustrates the main components of the system in accordance with embodiments of the invention in the context of a surgical table or operating room.

The present invention has utility as a system and process to accurately and efficiently define a position and orientation of a tool relative to a fiducial marker array, which will aid in a medical procedure. The following description of various embodiments of the invention is not intended to limit the invention to these specific embodiments, but rather to enable any person skilled in the art to make and use this invention through exemplary aspects thereof.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

As used herein, a fiducial marker refers to a point of reference detectable by a tracking system and may be, for example, an active transmitter, such as a light emitting diode (LED) or electromagnetic emitter; or a passive reflector, such as a plastic sphere with a retro-reflective film. In specific embodiments, the use of a particular type of fiducial marker is defined as such for those applicable embodiments. A fiducial marker array is an arrangement of two or more fiducial markers in a known geometric relationship in/on a rigid body of any geometric shape; an arrangement of three fiducial markers may be used to resolve all six degrees of freedom (6-DOF) of the rigid body, unless otherwise specified.

The term 'tool' can be any instrument capable of performing work on an external object. These illustratively include a probe, drill, cutter, burr, or saw blade; as well as any assembly used to house and/or operate the tissue contacting instrument (e.g. a cutter coupled to a drill and assembled in a housing, where the housing may be attached to the distal end of a robotic manipulator arm).

As used herein, the term 'communication' is to refer to the sending and/or receiving of data and/or energy either through a wireless or electrical connection.

Disclosed herein is the use of a tracking system. The tracking system includes at least one receiver to detect energy either emitted or reflected from a fiducial marker, where the receiver is coupled to a tracking module having a processor for processing a position and/or orientation (POSE) of a fiducial marker or fiducial marker array. The tracking module can generate a tool position based on the relationship between the fiducial marker array and the tool, where the relationship is determined using the calibration techniques described herein. In particular embodiments, the calibration technique uses a calibration device in communication with the tracking module to provide at least one reference point for determining the tool's position. The detectable energy can be for example but not limited to optical, electromagnetic, infrared, ultraviolet, magnetic, fiber optic, ultrasound and targeted visible light. An example of an optical tracking system is the Polaris Spectra® Optical Tracking System (NDI Medical). Also referenced herein are computer-assisted surgical systems, which are to be considered synonymous with computer-aided surgical systems, robotic surgical systems, navigation assisted surgical systems, image-guided surgical systems and the like.

As reference will be made to the ROBODOC™ Surgical System, it should be appreciated that any autonomous, haptic, or semi-autonomous robotic system either for medical or industrial applications can benefit from the device and methods disclosed herein. Examples of computer-assisted surgical systems that may benefit from the invention disclosed herein include for example the ROBODOC™ Surgical System (Think Surgical, Inc.), NavioPFS™ System (Blue Belt Technologies, Inc.), The RIO® Robotic System (Mako Surgical Corp.) a navigated freehand saw (TRAK Surgical), 4 degree of freedom saw, an articulating hand-held system with at least one degree of freedom, an articulating hand-held drilling system disclosed in provisional application 62/054,009 and incorporated herein by reference in its entirety, or any other computer-controlled device that requires tracking.

Embodiments of the present invention describe a system, device and methods to define a tool axis orientation and tool center point relative to a fiducial marker array to accurately track a tool to aid in a medical procedure. FIG. 1 depicts a high-level overview of a surgical system 101 to perform a computer-assisted surgery. Generally, a computer-assisted surgical system 103 includes a user interface 107 and tool 105, and is positioned to aid in a medical procedure on a patient 109. The user interface 107 may be a monitor to display user instructions such as, operating parameters, procedural workflow, the robotic state, functioning errors, guide commands, and a real-time view of a tool modifying tissue. The user interface 107 is also in certain embodiments a heads-up display unit (HUD), Google™ glasses, an external monitor, and/or a smart watch which may be electrically or wirelessly in communication with the robotic system. For example, a HUD is illustratively wirelessly connected to the robotic system via Bluetooth, TCP/IP, visible light communication, WLAN, or combination thereof. The robotic system and/or user interface may receive input from the user through the use of a controller device like a joystick, mobile phone, or by touching the monitor, or combination thereof. Such inputs may include for example guide commands, selecting various prompts given throughout a procedural workflow, selecting a certain medical procedure, designating the position of other external components/devices, aiding in registration of anatomy, configuring an optical tracking module, and combinations thereof. The surgical system 101 includes a tracking system 110 having detectors 112 coupled to a tracking module 111 to detect fiducial markers (203, 213 of FIG. 2) and track fiducial marker arrays (211 of FIG. 2) that may be positioned on the anatomy of interest, on the base of the surgical system 103, on the tool 105, on the calibration device 201, as well as on any other medical devices or reference locations to ensure the tool/s are accurately executing the procedure. Prior to surgery, a fiducial marker array is positioned and fixed with respect to the tool 105. The tool 105 is then calibrated using the methods described below so the tracking module 111 knows the exact location of the tool axis orientation and tool center point.

Figure 2A:
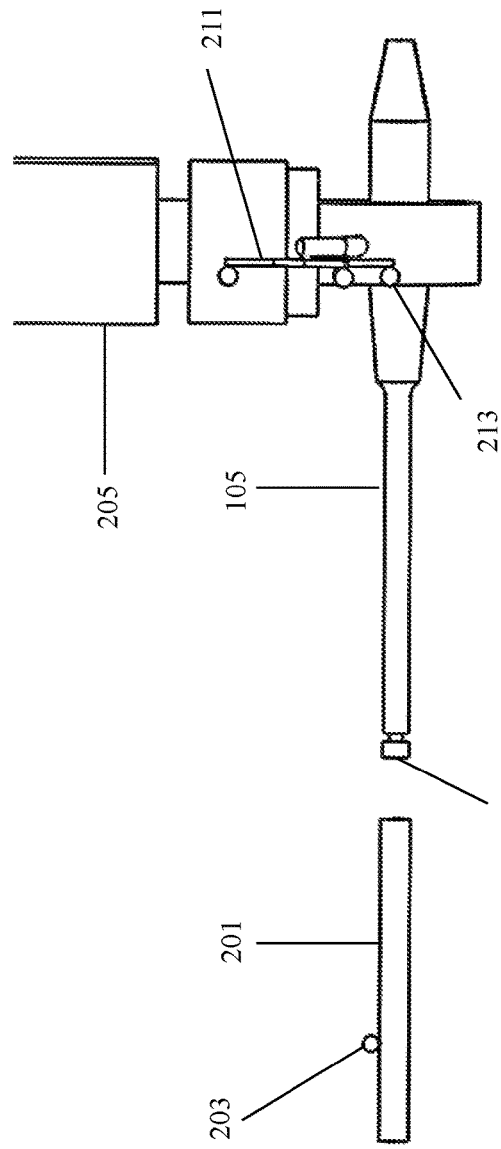
FIGS. 2A, 2B, and 2C depict a calibration device and method for defining a tool axis orientation relative to a fiducial marker array in accordance with embodiments of the invention.
Figure 2C:
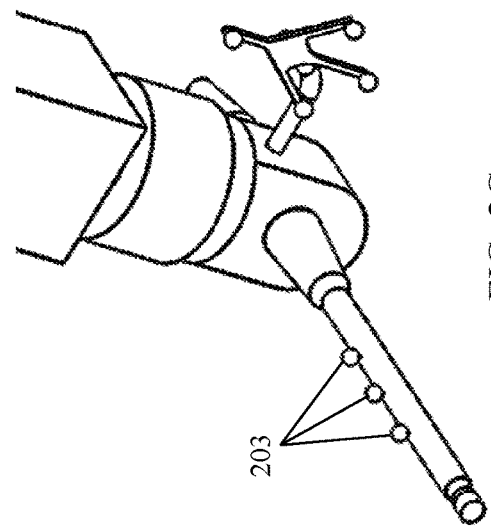
Figure 2B:
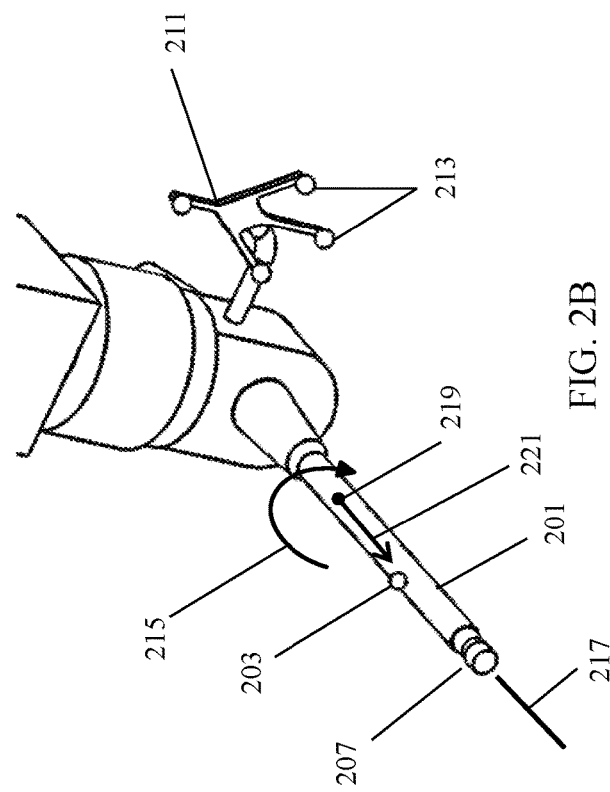
Figure 3:
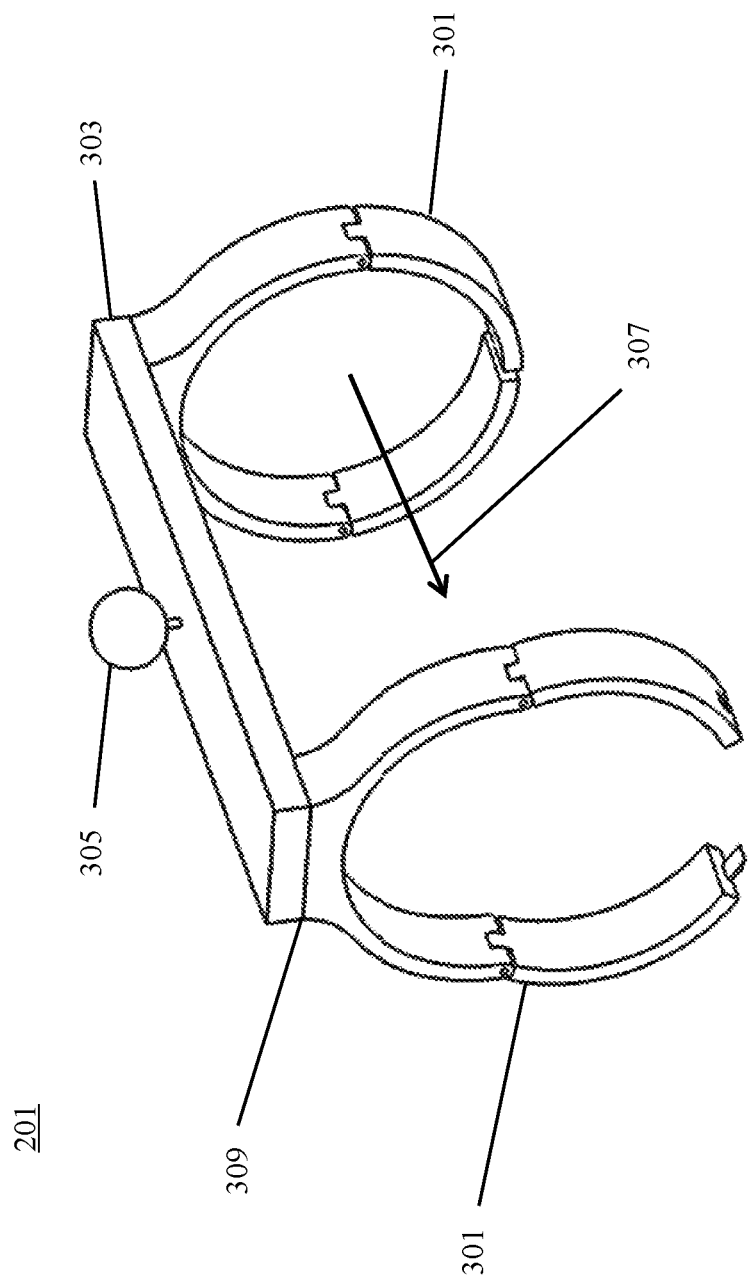
FIG. 3 depicts a calibration device capable of clipping onto a tool in accordance with embodiments of the invention.

An inventive embodiment of a device to quickly and more accurately calibrate a tool axis orientation relative to a fiducial marker array and tracking system is shown in FIGS. 2A-2C. FIG. 2A depicts a calibration device 201 in the shape of a hollow cylindrical sleeve that includes at least one fiducial marker 203. The fiducial marker 203 being either passive or active. The calibration device 201 may include two or more fiducial markers 203 positioned along the axis of the sleeve 201 as depicted in FIG. 2C. In another embodiment, with respect to FIG. 3, the calibration device 301 includes two or more attachment points or clips 311 capable of clipping onto a tool axis 307. A rigid member 303 assembled to the two or more attachment points or clips 311 has at least one fiducial marker 305 placed thereon, where the rigid member 303 is capable of rotating about the tool axis 307. The attachment clips 311 may come in varying diameters and may be modularly assembled to the rigid member 303. For example, clips 311 with different diameters may be assembled to the rigid member 303 at point 309, to accommodate tools of varying diameter. In a specific inventive embodiment, the attachment clips 311 loosely grasp the tool 105 to allow the entire calibration device 301 to freely rotate about the tool axis 307. In another specific embodiment, the attachment clips 311 include a bearing such that the clips may firmly grasp the tool and a bearing mechanism between the clip 311 and the rigid member 303 allows for the rigid member 303 to freely rotate about the attachment clips 311 and tool axis 307.

In specific embodiments, in order to define the tool axis 217 relative to the fiducial marker array 211, a fiducial marker array 211 includes a set of fiducial markers 213 in a known geometric relationship to resolve 6 degrees of freedom, where the fiducial marker array 211 is rigidly fixed to a tool 105. The tool 105 being attached to a distal end, link and or joint 205 of a computer controlled device. In a specific embodiment, the fiducial marker array 211 is incorporated and packaged with the tool 105, while in other embodiments the fiducial marker array is a separate entity, packaged separately, and is assembled and fixed to the tool 105 by a user in the operating room. The tool 105 may further have a working end with a tool tip surface and tool center point 207 to perform work on a workpiece. The calibration device is then placed on and/or clipped to the tool 105. The calibration device 201 may rotate freely (arrow 215) about the tool 105 but, in certain embodiments, cannot translate along the tool. In a specific embodiment, the calibration device 201 may be placed on the tool 105 such that gravity keeps the device against the end of the tool to prevent translation. The tool 105 and/or calibration device 201 may have a connection such as a rotary coupling to ensure translation does not occur. Additionally, the system may easily detect if the calibration device 201 has translated along the tool axis 217 during calibration and notify the user via a monitor, or audible alert for example.

In specific embodiments, the rotation may be done manually by a user who places the calibration device sleeve 201 on the tool 105 and rotates the calibration device 201 as the tracking system records the position of the fiducial marker 203 as it rotates. The calibration device 201 may have a handle, a grip, or an extruding portion that allows the user to easily rotate the calibration device 201 about the tool 105. In a specific embodiment, the calibration device 201 may automatically rotate about the tool 105. The calibration device 201 may have a connection on the proximal end that interacts with the tool 105. For example, the proximal end of the calibration device 201 may have a set of threads that screw into a portion of the tool 105 that is in communication with components such as motors, gears, actuators, rotary coupling, or any other conventional mechanical device that allows the calibration device 201 to automatically rotate about the tool 105. In a specific embodiment, the components to rotate the calibration device may include the same and/or similar elements used to operate the working end of the tool 105. Alternatively, the calibration device 201 includes a driver to automatically rotate itself about the tool 105. For example, the calibration device 201 may include multiple concentric sleeves wherein a first innermost sleeve remains stationary on the tool 105 and a second sleeve encompassing the first sleeve has a driver to rotate a fiducial marker 203 about the tool 105.

As the fiducial marker 203 rotates about the tool 105, the tracking system records the markers position throughout rotation. The fiducial marker 203 traces concentric circles of equal number to the number of fiducial markers. For example, one fiducial marker will trace a single concentric circle, while multiple fiducials as shown in FIG. 2B will trace multiple concentric circles along the axis of the calibration device 201. The tracking module 111 fits a circle to the positions recorded during rotation. The circle may be fitted to the data using algorithms such as a least squares methods including, but not limited to Gauss-Newton, Levenberg-Marquardt, Newton, variable projection, and orthogonal distance regression, Mahalanobis distance, or a combination thereof. It should be noted that only an arc of points is needed to model the data. The fitted circle has a center 219 on the tool axis and a normal vector 221, where the normal vector 221 represents the orientation of the tool axis 217. Therefore, the orientation of the tool axis can be defined relative to the fiducial marker array 211 based on the POSE of the fiducial marker array 211 with respect to the calculated normal vector 221.

In inventive embodiments where multiple fiducial markers 203 are used, then each circle will have a normal vector where the orientation of the tool axis 217 may be calculated by one or a combination of the following:
    i. The average of each of the tool vectors
    ii. The average of the vectors from one circle center to another
    iii. The average of i. and ii.

Thus by using multiple fiducial markers 203, the accuracy in defining the true orientation of the tool axis relative to the fiducial marker array 211 increases. As only one fiducial marker 203 is necessary to obtain the tool axis orientation relative to the fiducial marker array 211, multiple fiducial markers increases the accuracy of the calibration. Furthermore, by increasing the spacing between the fiducial markers along the tool axis 217 the accuracy of the calibration is improved when using the circle centers, where more information along a greater portion of the tool is captured. One primary advantage of the calibration devices described herein is there is no need to manufacture a precise geometric relationship between two or more of the fiducial markers 203 on the calibration device 201. Likewise, the tracking system does not need to resolve a full 6-DOF of the calibration device to accurately calibrate the tool to the tracking system (i.e. only one marker is technically needed to locate the tool axis orientation). In current systems, a precise geometric relationship between three or more fiducial markers is needed to accurately calibrate a tool. This increases manufacturing costs due to the required tolerances and can induce tracking errors where slight deviations in the geometric relationships occur during manufacturing.

In a specific embodiment, the processor may fit a cylindrical model to the calibration data. If a cylindrical model is used, then the calibration device may translate along the tool axis 217 where the tool axis 217 orientation may still be calculated. However, when using a cylindrical model, a subsequent step is needed to locate the tool center point as described below.

When fitting a circular or cylindrical model to the data, the algorithm may also account for the distribution of recorded positions as the fiducial marker 203 rotates about the tool 105. More data points may be collected in one position compared to another depending on the rotation speed or even how the user performs the calibration procedure. If more data points are collected during a particular part of the rotation compared to another, the circular or cylindrical model may be weighted towards the clustered region affecting the normal vectors and/or center points. Therefore, the algorithm may adjust the data such that an even distribution of points about the tool axis 217 is used to fit the circle or cylinder.

In a specific embodiment, one end of the calibration device 201 includes an abutment surface 401 as depicted in FIG. 4A. FIG. 4A is a cross-section view of the calibration device 201 placed about the axis of tool 105. One or more fiducial markers 203 are spaced a known distance 'd' from the abutment surface 401. When the calibration device 201 is placed over and/or clipped about the axis of the tool 105, the abutment surface 401 is coincident with the tool tip surface. If multiple fiducial markers 203 are used, then each of the fiducial markers 203 may be spaced at a known distance from the abutment surface 401. Although, only one of the fiducial markers 203 is required to have a known distance 'd' from the abutment surface 401, such as the most proximal or distal fiducial marker on the calibration device 201. In this embodiment, both the orientation of the tool axis 217 and the tool center point 207 of the working end may be defined relative to the fiducial marker array 211. The abutment surface 401 may be in full contact with the tool tip surface as shown in FIG. 4A or only a portion of the tool tip surface may be in contact with the abutment surface 401 as shown in FIG. 4B.

The fiducial marker array 211 capable of resolving 6 degrees of freedom is rigidly fixed to the tool 105. The calibration device 201 with the abutment surface 401 is placed on the tool 105 such that the abutment surface 401 is coincident with the tool tip surface. The calibration device 201 is rotated about the tool 105 and the tracking module calculates the normal vector 221 and tool axis orientation 217 using fitted circles as described above. The known distance from one or all fiducial markers on the sleeve to the abutment surface 401 is used to compute a plane that defines the end of the tool vector. For example, a plane is defined in space by the circle(s) traced by the fiducial marker(s) 203 at the position of the fiducial marker. By translating the circular plane the known distance from the fiducial marker(s) 203 to the abutment surface, a plane can be defined at the tool tip surface. The intersection of the plane defined at the tool tip surface and the normal vector calculated from the traced circular paths defines the tool tip center point 207 on the tool axis 217. Thus both the tool tip center point 207 of the working end of the tool and the orientation of the tool axis are defined relative to the fiducial marker array 211.

In a specific inventive embodiment, the tool center point 207 at the working end may be defined using a digitizer. Instead of having an abutment surface 401 on the calibration device 201, a plane at the tool tip surface is defined by digitizing a number of points on the tip of the tool. A digitizer generally includes a probe that is either mechanically or optically tracked to collect points in space relative to a coordinate system. The digitizer may be coupled to a robotic system as described in U.S. Pat. No. 6,033,415 which is incorporated by reference herein in its entirety. If the digitizer is coupled to the robotic system, a processor of the robotic system may perform the following calculations and communicate this information to the tracking module. If the digitizer is optically tracked, the tracking module may directly perform the following calculations. In this specific method embodiment, the orientation of the tool axis 217 relative to the fiducial marker array 211 can be determined using the embodiments described above. The tool tip center point 217 is determined by digitizing several points on the end of the tool 105, and a plane is best-fit to the digitized points using a processor or the tracking module. The tool tip center point position 207 is the intersection of the tool axis 217 defined by the calculated normal vector 221 to the traced circles, and the plane that is both perpendicular to the tool axis and best-fits the digitized points. Thus both the tool tip center point position 207 and the tool axis 217 are defined relative to the fiducial marker array 211.

The use of the calibration device 201 may further be used to check the calibration of a robotic computer-assisted surgical system. After performing any of the methods described in the previous embodiments, the robot may be actuated to move where the robot thinks the tool axis 217 is in robot coordinates. The calibration device 201 is then rotated with the tracking system recording the positions of fiducial marker(s) 203. A processor may fit a circle to the recorded positions of the fiducial marker. If the diameters of the circles fit to the traced paths, the centers of the circles fit to the traced paths, and the normal vectors of the circles fit to the traced paths all match within a specified tolerance those same parameters collected when the robot was originally calibrated then the calibration is valid. Likewise, if the diameters do not match, the centers do not match, the normal vectors do not match, or if the traced paths are not circular, then the calibration is invalid. This procedure may similarly be used to check the calibration of the entire robot.

Embodiments of the present invention also describe a method to locate a joint axis using a fiducial marker array. With respect to FIG. 5A, a link 501 distal to the target joint axis contains several fiducial markers 503 in sufficient number such that at least three fiducial markers 503 on the link are visible to the optical tracking system no matter the rotation angle of the link 501. The several fiducial markers 503 on the link 501 may be considered a fiducial marker array. The fiducial markers 503 are spaced such that 1) a coordinate system 507 may be established on the link 501 using only three visible fiducial markers 503 and 2) the known nominal geometry of the fiducial markers 503 may be used to establish the same coordinate system given any three visible fiducials. As the link 501 is rotated about its axis of rotation, the optical tracking system tracks the visible fiducials. Because, the link 501 has a constant axis of rotation, each fiducial traces a circular path about the axis of rotation. A processor may fit circles to the traced fiducial markers and calculate an approximate center 509 of the link axis. The average of the centers defines the position of the link axis in space. The processor may additionally calculate a normal vector to the fitted circle. The average of the normal vectors defines the orientation 511 of the link axis. In a specific embodiment, because at least three fiducials 503 are visible at all times, a fixed coordinate system may be established on the flange. Any two arbitrary points in space which are both fixed to the fiducial marker coordinate system 507 and fixed in global coordinate throughout rotation define the axis of rotation of the joint. Embodiments of the method find points that are on the instantaneous rotation axis of the object (the robot link). While there are an infinite number of points that are on the axis of rotation, only two need to be found to define the axis. The two points are both a) constant in the local link coordinate system and b) constant in the global coordinates assuming that proximal links are not being actuated.

Figure 5B:
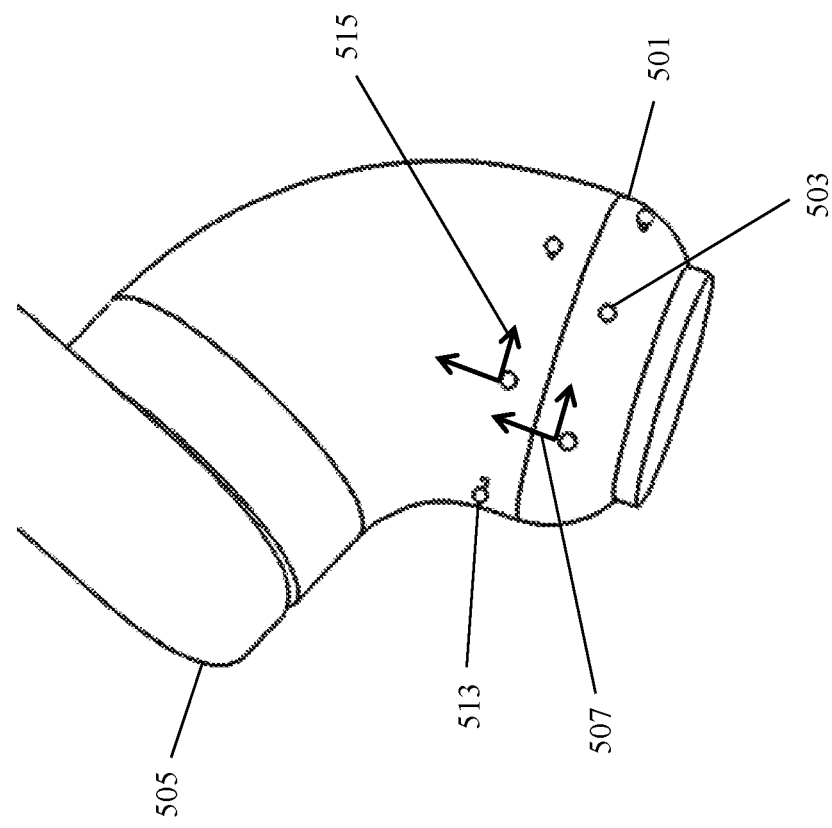
FIGS. 5A and 5B illustrate a method for determining a link axis and link rotation angle of a robot in accordance with embodiments of the invention.
Figure 5A:
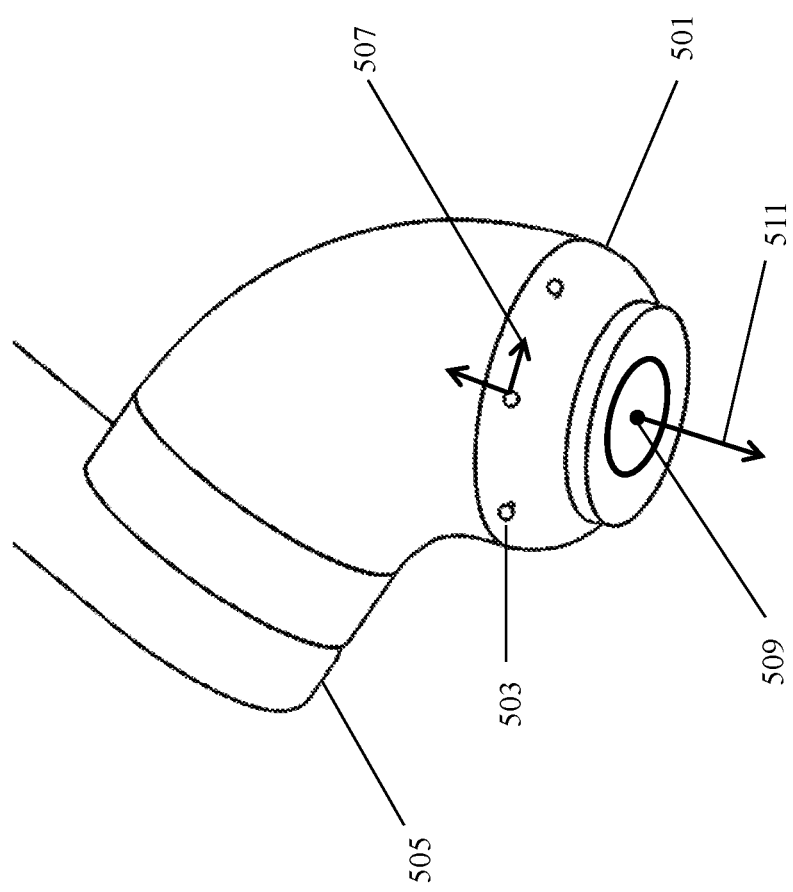

With respect to FIG. 5B, a second set of fiducial markers 513 may be placed just proximal of the distal link 501 to determine an absolute rotation angle between the two links. In one embodiment, the axis of rotation of the distal link is rotated relative to the proximal link to locate the axis of rotation as described in previous embodiments. Located on the proximal link, a similar set of fiducial markers 513 are positioned but with a different geometry such that the fiducials can be distinguished from the set of fiducial markers 503 on the distal link. The fiducial markers are spaced such that 1) a unique coordinate system 515 may be established on the flange using any three visible fiducials and 2) the known nominal geometry of the fiducial marker array may be used to establish the same coordinate system given any three visible fiducial markers. The angle between the two links may be determined by computing the relative rotation (i.e., projection angles) between the two coordinate systems about the axis of rotation of the link 501. The concept may be used for example to aid in calibrating a robot or used as an extra encoder. If fiducial marker arrays are positioned as described between and/or on each of the links, then the optical tracking system may define the position and orientation of the robot in any configuration. Therefore, a robot may be programmed to perform a calibration procedure where the optical tracking system may be used to measure the actual robot position and orientation compared to the programmed positions and orientations. In an alternative embodiment, any two arbitrary points in space which are constant in both the fiducial marker coordinate system 507 and the fiducial marker coordinate system of the proximal link 515 throughout rotation define the axis of rotation of the joint.

Figure 6:
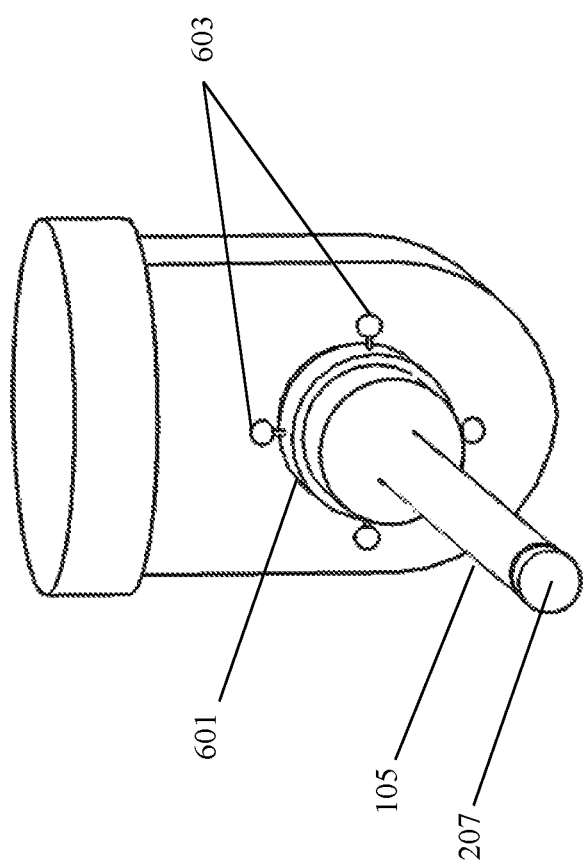
FIG. 6 depicts a rotating fiducial marker incorporated with a tool for tracking in accordance with embodiments of the invention.

Embodiments of the present invention also describe a system and method for tracking a tool using fiducial markers which rotate about a fixed axis as well as a more accurate method of registering a fiducial marker array with its corresponding nominal model. With respect to FIG. 6, a rotating object 601, with the axis of rotation of the rotating object aligned such that it is coincident with the axis of the tool 105, is fixed to the tool. At least one fiducial marker 603 is attached or incorporated with the rotating object. The rotating object rotates at a high velocity. The fiducial marker(s) are tracked by an optical tracking system which records multiple positions of the fiducial marker(s) such that a circular path is traced. In a specific embodiment, the optical receivers of the tracking module 111 are cameras where the circular path is traced throughout a series of camera frames. In a specific embodiment, the cameras may use a longer shutter speed such that the one or more fiducial markers trace one or more circular paths in a single frame.

A calibration device 201 may be used to define the orientation 217 of the tool axis and/or the tool center point 207 of the working end relative to the rotating fiducial markers 603 using any of the methods describe previously. If the sampling rate of the camera and the rotation rate of the fiducial marker(s) 603 are large, then the tool axis and tool tip position may be tracked using only the rotating fiducial marker(s) 603.

In a specific inventive embodiment, with the system including a rotating fiducial marker 603, a second marker array is attached to the tool with fiducial markers arranged in a geometry that is sufficient to resolve all six degrees of freedom of the tool. Although this marker array would not be used to track the tool axis and tool tip, the marker array may be used to track the overall geometry of the tool for other functions such as collision avoidance. In another embodiment, one or more fiducial markers are fixed to the tool rather than a full array sufficient to resolve all six degrees of freedom. Since knowing the tool axis and tool tip position resolves the movement of the system in five degrees of freedom, the one or more fixed fiducial markers can resolve the last degree of freedom (i.e., rotation about the tool axis).

Figure 7A:
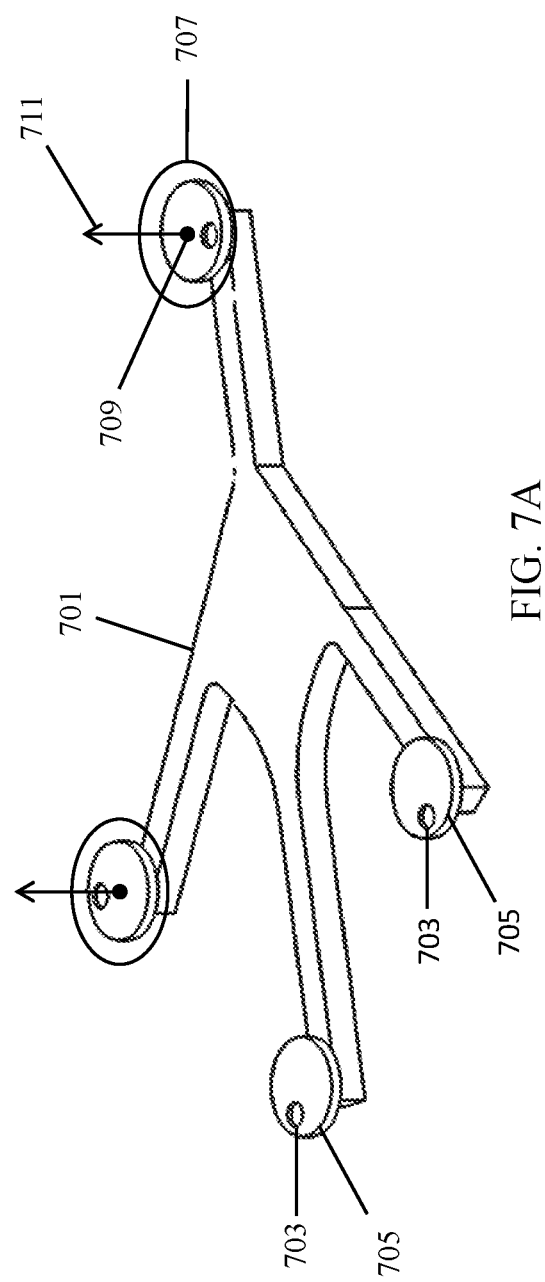
FIGS. 7A and 7B depict rotating fiducial markers on a fiducial marker array to improve tracking accuracy in accordance with embodiments of the invention.

In a specific embodiment of the present invention rotating fiducial markers on a fiducial marker array are utilized for improving the accuracy of tracking. With respect to FIGS. 7A and 7B, two fiducial marker array configurations 701 and 713 are shown. FIG. 7A depicts a fiducial marker array consisting of rotating bodies 705 with at least one fiducial marker 703 attached or incorporated therewith. Each rotational mechanism has zero mechanical play, such that each fiducial marker rotates 703 with constant radius with a center of rotation 709 that does not move on the marker array. In a specific embodiment, the tracking system 110 receivers are cameras. The tracking system 110 tracks using a camera shutter speed such that the shutter is open long enough to capture a substantial portion of each fiducial marker(s) circular travel 707, with a full rotation being ideal. For example, if the fiducial markers were rotating at 10,000 revolutions per minute (rpm), then a shutter speed of 0.006 seconds would capture a full rotation, while a shutter speed of 0.003 seconds would capture half a rotation. A processor then fits a circle in three dimensions to each circular path, and the center 709 and normal vectors 711 are computed for each circular path. A nominal model, consisting of nominal centers and normal vectors for each fiducial marker, may be registered to the computed centers and normal vectors, thus registering the marker array to a nominal model during tracking.

Figure 7B:
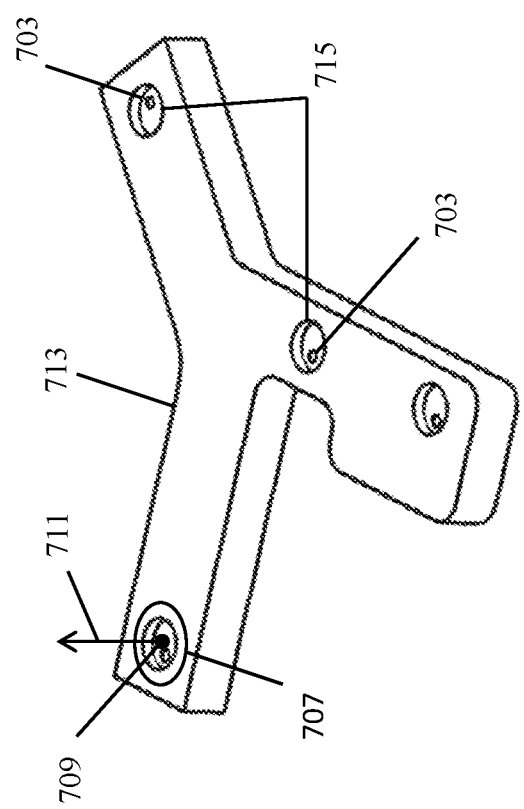

Similarly, FIG. 7B illustrates a different configuration of a marker array 713 where at least one fiducial marker 703 rotates about a center of rotation 709. In this embodiment, the fiducial marker is capable of rotating on its own rather than on a rotating platform. As before, the center 709 and normal vectors 711 may be calculated and registered to a nominal model consisting of nominal centers and normal vectors for each fiducial marker during tracking. This method results in increased accuracy as well as a more accurate registration as the exact center and normal vectors are computed and used for tracking and registration. It should also be appreciated that with this configuration only two fiducial markers are necessary to resolve 6 degrees of freedom. At least one rotating fiducial marker 703 and a second fiducial marker (not shown) fixed to the fiducial marker array 701 or 713. Additionally, by adding rotating fiducial markers, redundant tracking in multiple degrees of freedom is possible with a minimal amount of fiducial markers.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A calibration device comprising:
a body with an exterior surface, said body comprising two or more attachment points or clips joined with a rigid member, where said body is configured for placement on a tool having a tool axis such that said body can rotate about the tool axis;
one or two fiducial markers positioned on said rigid member affixed to the exterior surface of said body, where said one or two fiducial markers are tracked by a tracking system; and
wherein rotation of said calibration device allows for a determination of said tool axis.

2. The calibration device of claim 1 wherein said one or two fiducial markers are offset axially along a longitudinal axis of said body.

3. A calibration device comprising:
a body that is a hollow cylindrical sleeve with an exterior surface, said body configured for placement on a tool having a tool axis such that said body can rotate about the tool axis;
at least one fiducial marker affixed to the exterior surface of said body of said calibration device, where said at least one fiducial marker is tracked with a tracking system;
wherein rotation of said calibration device allows for a determination of said tool axis.

4. The calibration device of claim 3 wherein said at least one fiducial marker is positioned at a known distance from a first end of said hollow cylindrical sleeve.

5. The calibration device of claim 3 wherein said hollow cylindrical sleeve further comprises a first end with an abutment surface, and where a position of at least one fiducial marker of said at least one fiducial marker is a known distance from said abutment surface.

6. A surgical system comprising:
a tool having a tool axis;
a tracking system;
a fiducial marker array fixed to said tool and tracked by said tracking system;
a calibration device comprising a body with at least one fiducial marker positioned on said body, where said body is configured for placement on said tool such that said body can rotate about the tool axis; and
wherein in response to the rotation of said body one or more circular paths are generated by said at least one fiducial marker that are tracked by said tracking system, and said tracking system calculates at least one of a center point of the rotation or a normal vector to the circular path to define a tool axis orientation relative to said fiducial marker array fixed to said tool and to said tracking system.

7. The surgical system of claim 6 wherein said calibration device is a hollow cylindrical sleeve with two or more fiducial markers offset axially along a longitudinal axis of said hollow cylindrical sleeve.

8. A method for defining a position of a tool center point at a working end of a tool with respect to said fiducial marker array comprising:
providing the surgical system of claim 6 where the tracking system is used in the determination of:
a) an intersection of the normal vector of the one or more circular paths traced by said at least one fiducial marker at the center point of the rotation, and
b) a plane defined by an abutment surface on said calibration device that is a known distance from the fiducial marker.

9. A method for determining the tool axis orientation comprising:
providing the surgical system of claim 6 wherein said tracking system calculates at least one of:
a) the average of the normal vectors to the circular paths traced by two or more rotated fiducial markers,
b) the average of the normal vectors between the center points of the circular paths traced by the two or more rotated fiducial markers, or
c) the average of a and b.

10. A method for defining a tool axis relative to a fiducial marker array comprising:
fixing said fiducial marker array to a tool;
attaching a calibration device with at least one fiducial marker on the tool;
rotating said calibration device about the tools axis;
tracking the rotation of said at least one fiducial marker with a tracking system; and
calculating a normal vector and a center point from one or more circular paths traced by the fiducial marker rotation to define the tool axis orientation relative to the fiducial marker array.

11. The method of claim 10 further comprising:
collecting a set of points on a tool tip surface of said tool with a digitizer;
best-fitting a plane to the collected set of points with a processor; and
defining the position of a tool center point at said tool tip surface relative to the fiducial marker array from the intersection of the normal vector at the center point of rotation and the best-fit plane.

12. The method of claim 10 further comprising:
actuating a robot with said calibration device to a previously calibrated tool axis at a given robot position and orientation (pose);
rotating said calibration device about the tool axis;
recording the position of the fiducial marker during rotation with the tracking module;
fitting a circular model to the recorded positions with a processor;
calculating at least one of the circles diameter, center, or normal vector; and
comparing at least one of the circles diameter, center, or normal vector with the values stored from the previously calibrated tool axis to determine the robot calibration validity.

13. The method of claim 10 wherein one end of said calibration device further comprises a sleeve with an abutment surface whereby the fiducial marker on said sleeve is at a known distance from the abutment surface.

14. The method of claim 13 further comprising:
calculating the position of a tool center point at the working end of the tool based on the intersection of the calculated normal vector to the circular paths traced by the fiducial marker at the center point of rotation and a plane defined at the abutment surface.

15. A system for tracking a tool to aid in a medical procedure comprising:
a tool;
a tracking system;
a rotating body coincident about an axis of said tool, said rotating body comprising at least one fiducial marker such that said tracking system records a position of the at least one fiducial marker as the at least one fiducial marker rotates about the tool axis; and
a processor configured for calculating at least one of a vector normal to a fitted circle or a center point of the fitted circle.

16. The system of claim 15 wherein said processor is also programmed to fit a circle to the recorded positions of the fiducial marker.

17. The system of claim 15 wherein the tracking system records the position of the at least one fiducial marker during rotation and said processor is configured for fitting a circular model to the recorded positions and calculating at least one of a circle center or vector normal to the circle to define at least one of a distal link position or distal link orientation.

* * * * *